(12) United States Patent
Takatsuka et al.

(10) Patent No.: US 8,812,502 B2
(45) Date of Patent: Aug. 19, 2014

(54) CONTENT REPRODUCING APPARATUS, CONTENT REPRODUCTION METHOD, AND PROGRAM

(75) Inventors: Susumu Takatsuka, Tokyo (JP); Toru Sasaki, Tokyo (JP); Yuichi Sakai, Kanagawa (JP); Yoichiro Sako, Tokyo (JP); Toshiro Terauchi, Tokyo (JP); Hirofumi Tamori, Tokyo (JP); Makoto Inoue, Tokyo (JP); Katsuya Shirai, Kanagawa (JP); Kenichi Makino, Kanagawa (JP); Motoyuki Takai, Tokyo (JP); Takatoshi Nakamura, Kanagawa (JP); Akihiro Komori, Tokyo (JP); Akane Sano, Tokyo (JP)

(73) Assignee: Sony Corporation, Tokyo (JP)

( * ) Notice: Subject to any disclaimer, the term of this patent is extended or adjusted under 35 U.S.C. 154(b) by 726 days.

(21) Appl. No.: 12/160,819

(22) PCT Filed: Jan. 11, 2007

(86) PCT No.: PCT/JP2007/050634
§ 371 (c)(1),
(2), (4) Date: Feb. 27, 2009

(87) PCT Pub. No.: WO2007/081049
PCT Pub. Date: Jul. 19, 2007

(65) Prior Publication Data
US 2010/0168879 A1    Jul. 1, 2010

(30) Foreign Application Priority Data
Jan. 13, 2006    (JP) .................................. 2006-006256

(51) Int. Cl.
*G06F 7/00*    (2006.01)
*G06F 17/00*   (2006.01)

(52) U.S. Cl.
USPC ........................... 707/737; 707/748; 707/752

(58) Field of Classification Search
USPC ............................................. 707/737, 748, 752
See application file for complete search history.

(56) References Cited

U.S. PATENT DOCUMENTS

7,102,067 B2 *   9/2006    Gang et al. ....................... 84/600
7,135,637 B2 *   11/2006   Nishitani et al. ................ 84/723

(Continued)

FOREIGN PATENT DOCUMENTS

JP    2003 317451    11/2003
JP    2004 113552    4/2004

(Continued)

OTHER PUBLICATIONS

Jean-Julien Aucouturier, et al., "Scaling Up Music Playlist Generation", Multimedia and Expo, ICME '02 Proceedings, IEEE International Conference, vol. 1, XP010604317, Aug. 26, 2002, pp. 105-108.

(Continued)

*Primary Examiner* — Usmaan Saeed
*Assistant Examiner* — Paul Kim
(74) *Attorney, Agent, or Firm* — Oblon, Spivak, McClelland, Maier & Neustadt, L.L.P.

(57) ABSTRACT

Music contents assigned to play lists are reproduced so as to correspond to user's preference. A music content database 7 has stored a plurality of music contents. A CPU 3 creates genre ranks such that music contents that have been more frequently, for example, reproduced are more highly ranked. In addition, the CPU 3 creates play lists corresponding, for example, to tempos and stores the created play lists in a play list database 8. The CPU 3 selects a play list corresponding to a moving tempo obtained from a tempo detection section 9 and selects music content categorized as a highly ranked genre in the genre ranks from those corresponding to the selected play list. The selected music content is supplied to a decoder and amplifier section 12 and then reproduced from a head phone 14.

12 Claims, 5 Drawing Sheets

(56) References Cited

U.S. PATENT DOCUMENTS

| | | |
|---|---|---|
| 2005/0126370 A1 | 6/2005 | Takai et al. |
| 2007/0154872 A1 | 7/2007 | Sako et al. |
| 2007/0157798 A1 | 7/2007 | Sako et al. |
| 2007/0186756 A1 | 8/2007 | Sano et al. |
| 2007/0221045 A1 | 9/2007 | Terauchi et al. |
| 2007/0261538 A1 | 11/2007 | Takai et al. |

FOREIGN PATENT DOCUMENTS

| | | | |
|---|---|---|---|
| JP | 2005 156641 | 6/2005 | |
| JP | 2005 526340 | 9/2005 | |
| JP | 2005 276400 | 10/2005 | |
| WO | 03/019560 A2 | 3/2003 | |
| WO | WO 2005082471 * | 2/2004 | ............. A63B 69/00 |
| WO | 2005/082471 A1 | 9/2005 | |

OTHER PUBLICATIONS

R. W. Picard, et al., "Affective Wearables", Wearable Computers, Digest of Papers, First International Sympo Sium, XP010251547, Oct. 13, 1997, pp. 90-97.

U.S. Appl. No. 12/160,452, filed Jul. 10, 2008, Takatsuka, et al.

\* cited by examiner

Fig. 2

GENRE RANKS OF USER A

| 1 | Rock |
|---|---|
| 2 | Alternative |
| 3 | Hip Hop |
| 4 | R&B |
| 5 | Blues |

CONTENT REPRODUCING APPARATUS, CONTENT REPRODUCTION METHOD, AND PROGRAM

TECHNICAL FIELD

The present invention relates to a content reproducing apparatus, a content reproducing method, and a program.

BACKGROUND ART

Some reproducing apparatus that reproduce music content have a function called a play list with which a user can freely designate a reproduction order of a plurality of music contents. A play list can be freely edited and stored in a file. Thus, the user can store his or her designated reproduction order of his or her favorite music contents and listen to them in the stored reproduction order at any time.

Moreover, in recent years, a technique of categorizing music contents based on their characteristics such as song name, artist name, genre, tempo, released year, number of reproduction times, and so forth and automatically creating a list of contents including common characteristics has been proposed (refer to Japanese Patent Application Laid-Open (translation version of PCT international publication) No. 2005-526340). This list that was created in such a manner is also referred to as a play list. As storage (record) capacities of hard disks, optical discs, and semiconductor memories are increasing, it is becoming difficult for the user to know whole music contents stored (recorded) thereon. In this situation, with a play list, the user can easily listen to his or her desired music contents.

If the user wants to listen to music content A that was released in 1998, it is rare that he or she exactly memorizes its released year. In this situation, if a play list such as "the last half of the 90s" has been created, he or she can listen to music content A by selecting the play list and performing the reproduction process.

Moreover, in recent years, a technique of changing reproduction modes of music contents corresponding to the user's body motions has been proposed. Japanese Patent Application Laid-Open No. 2005-156641 publication describes a reproduction mode controlling apparatus that detects user's walking and running tempos and changes the reproduction speeds of music contents corresponding to the detected tempos.

As the storage capacity of record mediums increases, the number of music contents stored thereon increases. Thus, the quantity (number) of music contents assigned to one play list increases. For example, to allow a play list to deal with human's ambiguous memory like the foregoing released year, the play list has to have a margin of common characteristics of music contents such as "the last half of the 90s" instead of strictly "1998". Thus, the number of music contents corresponding to one play list becomes large.

Normally, when a plurality of music contents is assigned to one play list, the reproducing apparatus side properly shuffles the music contents and reproduces them at random. Thus, it was likely that music contents to which the user wants to listen is not reproduced, namely music contents corresponding to user's preference are not reproduced. Although the user can manually select his or her favorite music content, if he or she is walking or running, it is difficult for him or her to perform such an operation.

DISCLOSURE OF THE INVENTION

Therefore, an object of the present invention is to provide a content reproducing apparatus, a content reproducing method, and a program that determine music content corresponding to user's preference from those assigned to a play list and preferentially reproduce the determined music content.

To solve the foregoing problem, the present invention is a content reproducing apparatus, comprising:

a content storage section which stores a plurality of contents;

a rank information creating section which creates rank information based on user's preference information;

a rank information storage section which stores the rank information;

a play list creating section which assigns the plurality of contents to play lists to create the play lists; and a reproduction controlling section which reproduces the contents assigned to the play lists in an order based on the rank information.

In addition, the present invention is a content reproducing method, comprising:

a content storing step for storing a plurality of contents;

a rank information creating step for creating rank information based on user's preference information;

a rank information storage step for storing the rank information;

a play list creating step for assigning the plurality of contents to play lists and creating the play lists; and a reproduction controlling step for reproducing the contents assigned to the play lists in the order based on the rank information.

In addition, the present invention is a program which causes a computer to execute:

a content storing step for storing a plurality of contents;

a rank information creating step for creating rank information based on user's preference information;

a rank information storage step for storing the rank information;

a play list creating step for assigning the plurality of contents to play lists to create the play lists; and a reproduction controlling step for reproducing the contents assigned to the play lists in an order based on the rank information.

According to the present invention, music content corresponding to user's preference can be selected from a plurality of music contents assigned to a play list. The selected music content can be preferentially reproduced.

BEST MODES FOR CARRYING OUT THE INVENTION

Figure 1:
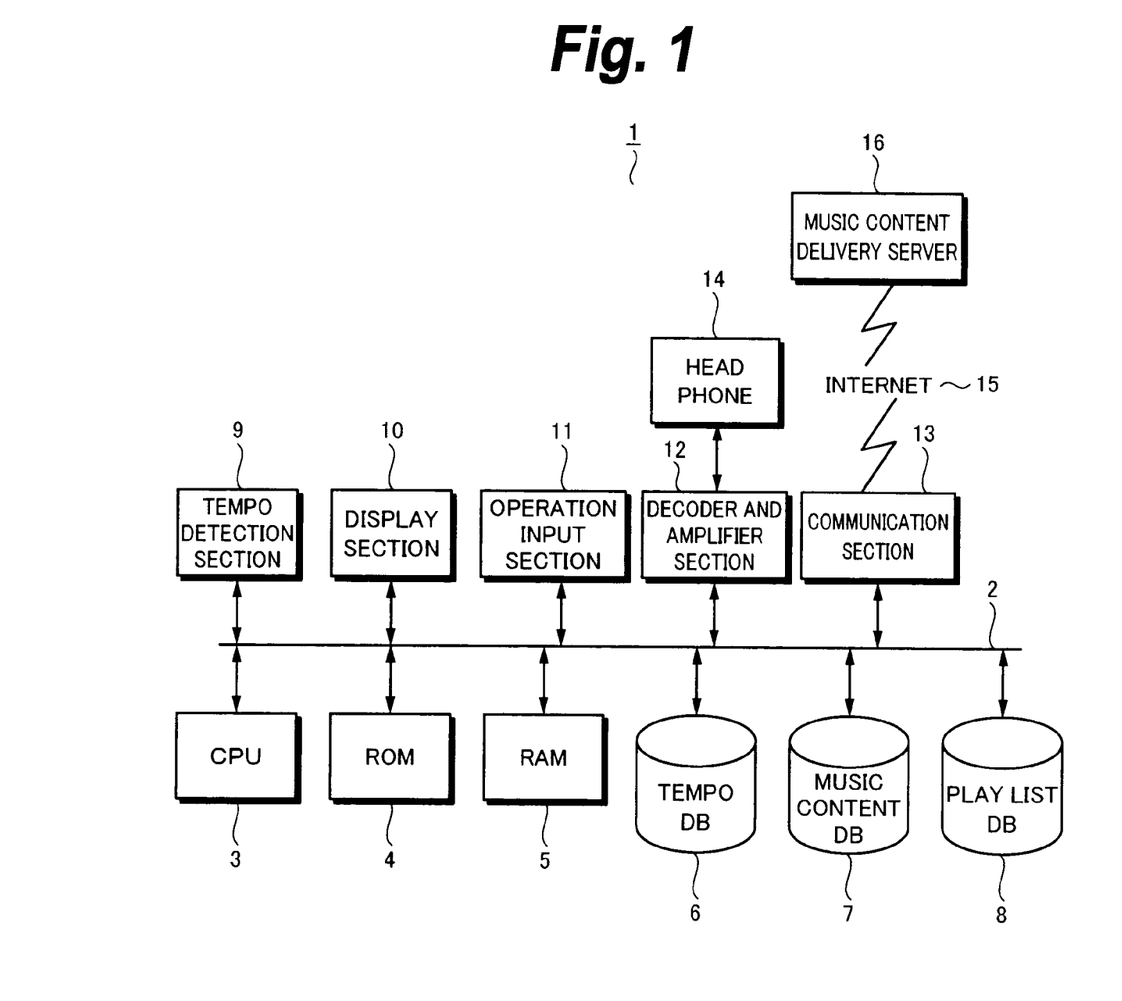
FIG. 1 is a block diagram showing a structure of a content reproducing apparatus according to an embodiment of the present invention.

Next, with reference to the accompanying drawings, an embodiment of the present invention will be described. FIG.

1 shows a structure of a content reproducing apparatus 1 according to the embodiment of the present invention. Connected to a bus 2 of the content reproducing apparatus 1 are a CPU (Central Processing Unit) 3, a ROM (Read Only Memory) 4, a RAM (Random Access Memory) 5, a tempo database (database is abbreviate as DB in the drawing) 6, a music content database 7, a play list database 8, a tempo detection section 9, a display section 10, an operation input section 11, a decoder and amplifier section 12, and a communication section 13. The decoder and amplifier section 12 is also connected to a head phone 14. In this embodiment, the content reproducing apparatus 1 is of a portable type. With the content reproducing apparatus 1, the user can listen to music content while he or she is moving such as walking, running, or exercising.

Next, the structure of the content reproducing apparatus 1 will be described in detail. The CPU 3 that is an example of the reproduction control section controls each section of the content reproducing apparatus 1 by executing a program stored in the ROM 4. For example, as will be described later, the CPU 3 changes the reproduction order of music contents assigned to a play list and reproduces them in the changed order. The RAM 5 is used as a work area with which the CPU 3 executes the program. In addition, the RAM 5 is also used as means for temporarily storing data generated in each process.

The tempo database 6 has stored moving tempos such as user's walking tempo and running tempo (hereinafter referred to as a moving tempo) detected by the tempo detection section 9. When a moving tempo detected by the tempo detection section 9 varies for a predetermined amount or more, a moving tempo stored in the tempo database 6 is changed.

The music content database 7 as an example of a content storage section associatively stores a plurality of music contents and their meta information. Herein, meta information is data that describe an attribute of each music content. Meta information is, for example, song name, tempo, number of reproduction times, genre, performing duration, performer(s), and so forth of each music content.

A plurality of play lists created under the control of the CPU 3 are stored in the play list database 8.

Moreover, in this embodiment, rank information is stored in the music content database 7 or the play list database 8. Rank information is information that represents priority assigned corresponding to user's preference for categories such as genre and artist. As will be described later, in a selected play list, music contents are reproduced in the order based on the rank information. In addition, in this embodiment, rank information of music information corresponding to genres (hereinafter, appropriately referred to as genre ranks) will be exemplified.

Figure 2:
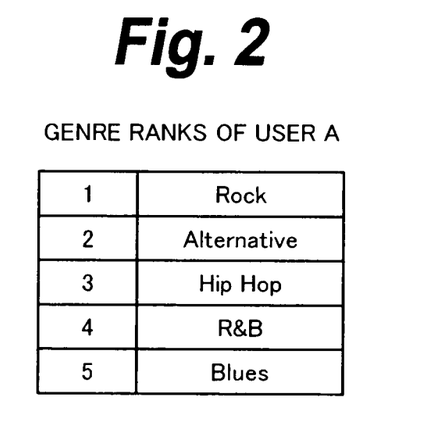
FIG. 2 is a schematic diagram showing exemplary genre ranks according to an embodiment of the present invention.

With reference to meta information of individual music contents, the CPU 3 determines genres of music contents that have been frequently reproduced, assigns priority to the music contents such that genres of music contents that have been more frequently reproduced are highly ranked, and creates genre ranks. FIG. 2 shows exemplary genre ranks of user A in this embodiment. The genre ranks show that user A has most frequently listened to music contents categorized as a genre of rock and has second most frequently listened to music contents categorized as a genre of alternative music. The genre ranks also show that user A has third most frequently listened to music contents categorized as a genre of hip hop, followed by music contents categorized as a genre of R & B (that is an abbreviated music genre of rhythm and blues), followed by music contents categorized as a genre of blues.

Of course, since the genre ranks shown in FIG. 2 are exemplary, other genres including Enka (Japanese popular songs) and pops may be assigned priority. Genre ranks may also be created such that genres to which more music contents belong in those stored in the music content database 7 are highly ranked instead of genre ranks created corresponding to music contents that have been frequently reproduced. Instead, the user may manually input genre priority with the operation input section 11 and the CPU 3 may create genre ranks corresponding thereto. The genre ranks created in such a manner are stored in the music content database 7 or the play list database 8.

The tempo database 6, the music content database 7, and the play list database 8 are composed, for example, of hard disks. In addition, a hard disk for storing rank information such as genre ranks may also be disposed. In addition, the storage area of one hard disk may be divided into areas for moving tempos, music contents, play lists, and rank information.

The music content database 7 may be composed, for example, of a semiconductor memory or an optical disc that can be freely attached to and detached from the content reproducing apparatus 1 instead of the hard disks that are built in the content reproducing apparatus 1.

Returning back to FIG. 1, the content reproducing apparatus 1 will be further described. The tempo detection section 9 is composed of an acceleration sensor mounted, for example, on the main body of the content reproducing apparatus 1 or the head phone 14. The tempo detection section 9 detects a user's moving tempo. The moving tempo is defined as the mean number of time intervals T after one foot touches the ground until the other foot touches it for a predetermined time period, for example, one minute, in other words, the number of foot steps per minute. Thus, when the user is moving, for example, walking or running at fast speed, the number of foot steps per minute is large.

For example, when a male adult walks at a slow pace, the moving tempo is around 105 foot steps/minute to 110 foot steps/minute. When he runs at a fast pace, the moving tempo is in the range around from 120 foot steps/minute to 125 foot steps/minute. Experimental results show that the moving tempos of humans are in the range around from 60 to 250 (foot steps/minute) and that the tempos in their unintentional walking state vary within around several %. In addition, it is known that there is a difference of around 70 foot steps/minute in the moving tempos between a normal walking state and a full speed running state although it depends on person by person.

In addition, in a tune as music content, a tempo is the length of a beat, that is, the speed of a meter. Herein, a meter is a basic rhythm at each equal interval of music content. A beat is one time unit. The length of a meter depends on music content, but may change in the same music content. In this specification, as the unit of a tempo, unit BPM (Beat per Minute) that represents the mean number of quarter notes per minute is used.

Moreover, the tempo detection section 9 performs a process of correlating the tempo of the song in the unit of BPM with the detected moving tempo. In this case, the moving tempo may not be correlated with the tempo of the song in the ratio of 1 to 1. Instead, the moving tempo may be multiplied by a proper correction coefficient and then compared with the tempo of the song. The process of correlating the moving tempo with the tempo of the song may be executed by the CPU 3.

In addition, the tempo detection section 9 is not limited to an acceleration sensor, but may be a speed sensor, a pressure sensor, a body motion acceleration sensor, a position sensor, or the like. Instead, the tempo detection section 9 may detect biological information of, for example, heart rate, skin perspiration, skin resistance, muscle potential, or body surface temperature of the user to detect the moving tempo of the user on the basis of the biological information. The tempo detection section 9 may be separated from the content reproducing apparatus 1. In this case, the tempo detection section 9 may wirelessly communicate with the content reproducing apparatus 1 to supply the moving tempo to the content reproducing apparatus 1.

The display section 10 is composed, for example, of an LCD (Liquid Crystal Display). The display section 10 displays various types of information based on operations of the content reproducing apparatus 1. The display section 10 displays, for example, reproduction position information, song name, and so forth of music content.

The operation input section 11 is composed of buttons and so forth disposed on the housing of the content reproducing apparatus 1 and a remote control device connected wirelessly or with a cable to the content reproducing apparatus 1. With the operation input section 11, music content can be, for example, reproduced, fast-forwarded, and rewound. In addition, with the operation input section 11, the user can freely create a play list. Instead, the forgoing display section 10 may be composed of a touch panel that functions as the operation input section.

The decoder and amplifier section 12 decodes data of music content supplied from the music content database 7 and performs a D/A (Digital to Analog) conversion for the decoded data of music content. Data of music content that have been converted into an analog signal are amplified and supplied to the head phone 14. Music content is reproduced through the head phone 14.

The communication section 13 has functions of both an interface for connecting the content reproducing apparatus 1 to a music content server 16 and an interface for connecting the content reproducing apparatus 1 with an external device such as a personal computer. The communication section 13 can be connected, for example, to the music content delivery server 16 through the Internet 15, to communicate with the music content delivery server 16, and caused to download music content from the music content delivery server 16. When necessary, a file conversion process and an encoding process are performed for the downloaded music content. The processed music content is stored and registered in the music content database 7. The content reproducing apparatus 1 can be connected to a personal computer, for example, through a USB of the communication section 13. Music content ripped from a record medium such as an optical disc can be transferred from the personal computer to the content reproducing apparatus 1.

Figure 3:
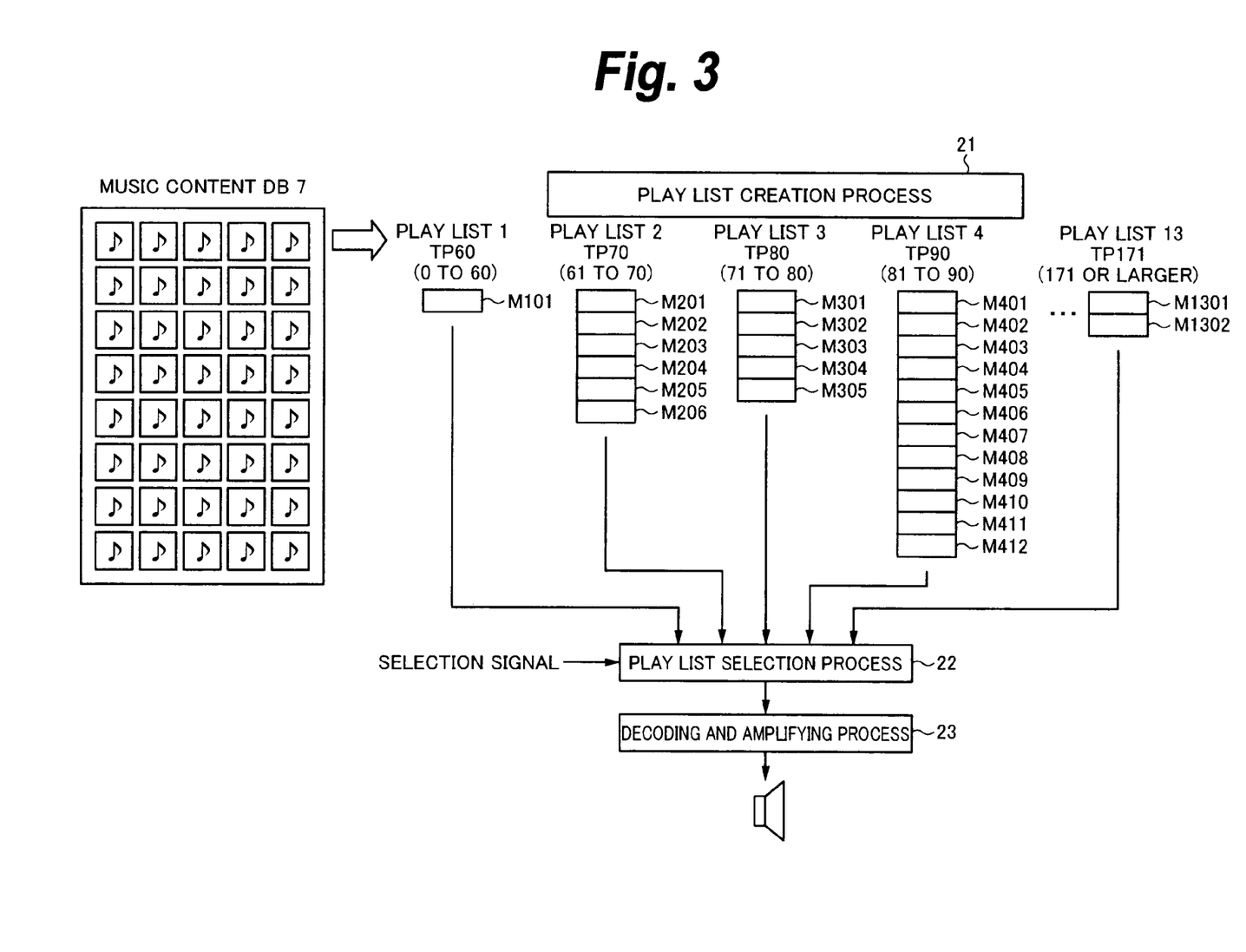
FIG. 3 is a schematic diagram showing an example of a process of a content reproducing apparatus according to an embodiment of the present invention.

Next, with reference to FIG. 3 and FIG. 4, an example of the operation of the content reproducing apparatus 1 will be described. First, a play list selection process 21 is performed. As shown in FIG. 3, the music content database 7 has stored a plurality of music contents (represented by musical notes in FIG. 3). In the play list creation process 21, a play list is created in such a manner that music contents are assigned on the basis of tempo information of meta information stored in association therewith.

Play list 1 is created with music contents having tempos in the range, for example, from 0 to 60 BPM. In addition, play list 2 is created by music contents having tempos in the range, for example, from 61 to 70 BPM. In addition, play list 3 is created by music contents having tempos in the range, for example, from 71 to 80 BPM. In addition, play list 4 is created by music contents having tempos in the range, for example, from 81 to 90 BPM. Likewise, play lists are created by music contents having tempos that increment by 10 BPM. Play list 13 is created by music contents having tempos of 171 BPM or higher. In FIG. 3, for simplicity, play lists 5 to 12 are omitted.

For example, music content M101 having a tempo of 55 BPM contained in meta information is assigned to play list 1. Music content M201 having a tempo of 67 BPM is assigned to play list 2. Music content M301 having a tempo of 74 BPM is assigned to play list 3. Music content M401 having a tempo of 82 BPM is assigned to play list 4. In addition, music content M1301 having a tempo of 175 BPM is assigned to play list 13. As shown in FIG. 3, in this embodiment, music content M101 is assigned to play list 1, music contents M201 to M206 are assigned to play list 2, music contents M301 to M305 are assigned to play list 3, music contents M401 to M412 are assigned to play list 4. In addition, it is assumed that music contents M1301 and M1302 are assigned to play list 13.

Moreover, meta information is added to each play list. Meta information represents a characteristic of each play list. For example, meta information TP60 is added to play list 1. Meta information TP60 denotes that music contents having tempos in the range from 0 to 60 BPM are assigned to play list 1. Meta information TP70 is added to play list 2. Meta information TP70 denotes that music contents having tempos in the range from 61 to 70 BPM are assigned to play list 2. Meta information TP80 is added to play list 3. Meta information TP80 denotes that music contents having tempos in the range from 71 to 80 BPM are assigned to play list 3. Meta information TP90 is added to play list 4. Meta information TP90 denotes that music contents having tempos in the range from 81 to 90 BPM are assigned to play list 4. Meta information TP171 is added to play list 13. Meta information TP171 denotes that music contents having tempos of 171 BPM or larger are assigned to play list 13.

A play list created in the play list creation process 21 is stored in the play list database 8 along with meta information added to the play list.

Thereafter, a play list selection process 22 is performed. The play list selection process 22 is a process controlled with a selection signal generated by the CPU 3 corresponding to information supplied from the tempo detection section 9.

Figure 4:
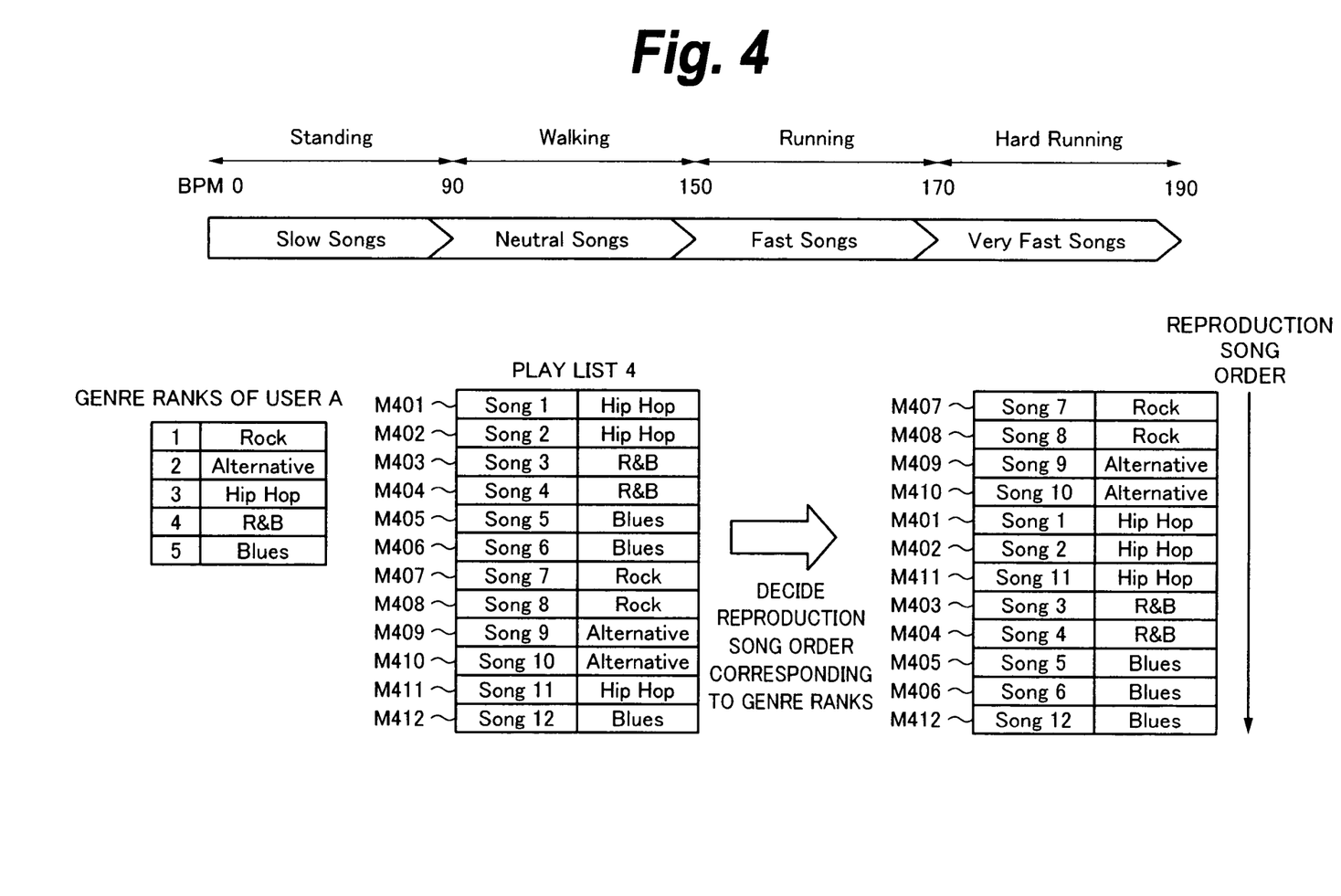
FIG. 4 is a schematic diagram describing an example of a play list corresponding to a user's moving tempo.

FIG. 4 shows an example of changes of moving states of a human from a stop state, to a walking state in which he or she is gradually increasing the walking speed, to a running state. In a standing state in which a human is stopping or walking very slowly, the tempo detection section 9 detects a moving tempo ranging around from 0 to 90 BPM and selects a play list corresponding to the detected moving tempo. In FIG. 4, one or a plurality of play lists selected in the range from 0 to 90 BPM are generically named slow songs. In a walking state in which a human is walking, the tempo detection section 9 detects a tempo around ranging from 91 to 150 BPM and selects a play list corresponding to the detected moving tempo. In FIG. 4, one or a plurality of play lists selected in the range from 91 to 150 BPM are generically named neutral songs.

In a running state in which a human is running, the tempo detection section 9 detects a moving tempo ranging around from 151 to 170 BPM and selects a play list corresponding to the detected moving tempo. In FIG. 4, one or a plurality of play lists selected in the range from 151 to 170 BPM are generically named fast songs. In a hard running state in which a human is running at full speed, the tempo detection section 9 detects a moving tempo ranging around from 171 BPM to 190 BPM and selects a play list corresponding to the detected tempo. In FIG. 4, one or a plurality of play lists selected in the range from 171 BPM to 190 BPM are generically named very fast songs.

A play list is selected corresponding to a moving tempo detected in the tempo detection section 9. When a tempo in the range from 0 to 60 BPM is obtained as a moving tempo of the user, play list 1 is selected and music contents corresponding to play list 1 are reproduced. When a tempo in the range from 61 to 70 BPM is obtained as a moving tempo of the user, play list 2 is selected and music contents corresponding to play list 2 are reproduced. When a tempo in the range from 71 to 80 BPM is obtained as a moving tempo of the user, play list 3 is selected and music contents corresponding to play list 3 are reproduced. Likewise, when another moving tempo is obtained, a play list corresponding to the obtained user's moving tempo is selected and music contents corresponding to the selected play list are reproduced.

For example, it is assumed that the tempo detection section 9 obtains 88 BPM as a moving tempo of the user. The detected moving tempo (88 BPM) is supplied to the CPU 3. Since the moving tempo supplied from the tempo detection section 9 is 88 BPM, the CPU 3 generates a selection signal that causes a play list corresponding to meta information TP90 to be selected from those stored in the play list database 8. The generated selection signal causes play list 4 corresponding to meta information TP90 to be selected.

Moreover, in the play list selection process 22, a process of controlling the reproduction order of music contents assigned to the selected play list is performed. Conventionally, the reproduction order of music contents M401 to M412 assigned to play list 4 was randomly changed and they were reproduced in the changed reproduction order. Thus, there was a risk of which music content to which the user wants to listen cannot be quickly reproduced. In contrast, according to the present invention, since rank information such as genre ranks represents user's preference, music contents assigned to a play list are selected and reproduced in the order on the basis of the rank information.

As shown in FIG. 4, when play list 4 is selected, the CPU 3 decides the reproduction song order of music contents M401 to M412 assigned to play list 4 based on genre ranks. In the genre ranks, rock has the highest priority. Thus, the reproduction song order is set such that music contents M407 and M408 categorized as a genre of rock are preferentially reproduced from those of play list 4. In the genre ranks, alternative has the next highest priority. Thus, reproduction song order is set such that music contents M409 and M410 categorized as a genre of alternative are reproduced after them. Likewise, reproduction song order is set such that music contents categorized as highly ranked genres are preferentially reproduced. In other words, reproduction song order is set such that music contents categorized as genres of hip hop, R & B, and blues having priority in this order in genre ranks are reproduced. In such a manner, the reproduction song order of music contents M401 to M412 assigned to play list 4 is decided.

Thereafter, the CPU 3 selects music content M407 based on the decided reproduction order and supplies the selected music content M407 to the decoder and amplifier section 12. The decoder and amplifier section 12 performs a decoding and amplifying process 23 for the supplied music content M407 and supplies the music content M407 that have been processed for the decoding and amplifying process 23 to the head phone 14. The music content is reproduced through the head phone 14. After the reproduction of music content M407 has been completed, the CPU 3 selects music content M408 which comes to next in play list 4 from those of play list 4 and supplies the selected music content M408 to the decoder and amplifier section 12. The decoder and amplifier section 12 performs the decoding and amplifying process 23 for music content M408 and the music content M408 is reproduced. In such a manner, music contents corresponding to play list 4 are successively reproduced in the order based on the genre ranks.

In such a manner, the user can reproduce music contents having nearly the same tempo as his or her moving tempo in the order based on genre ranks corresponding to the user's preference.

Figure 5:
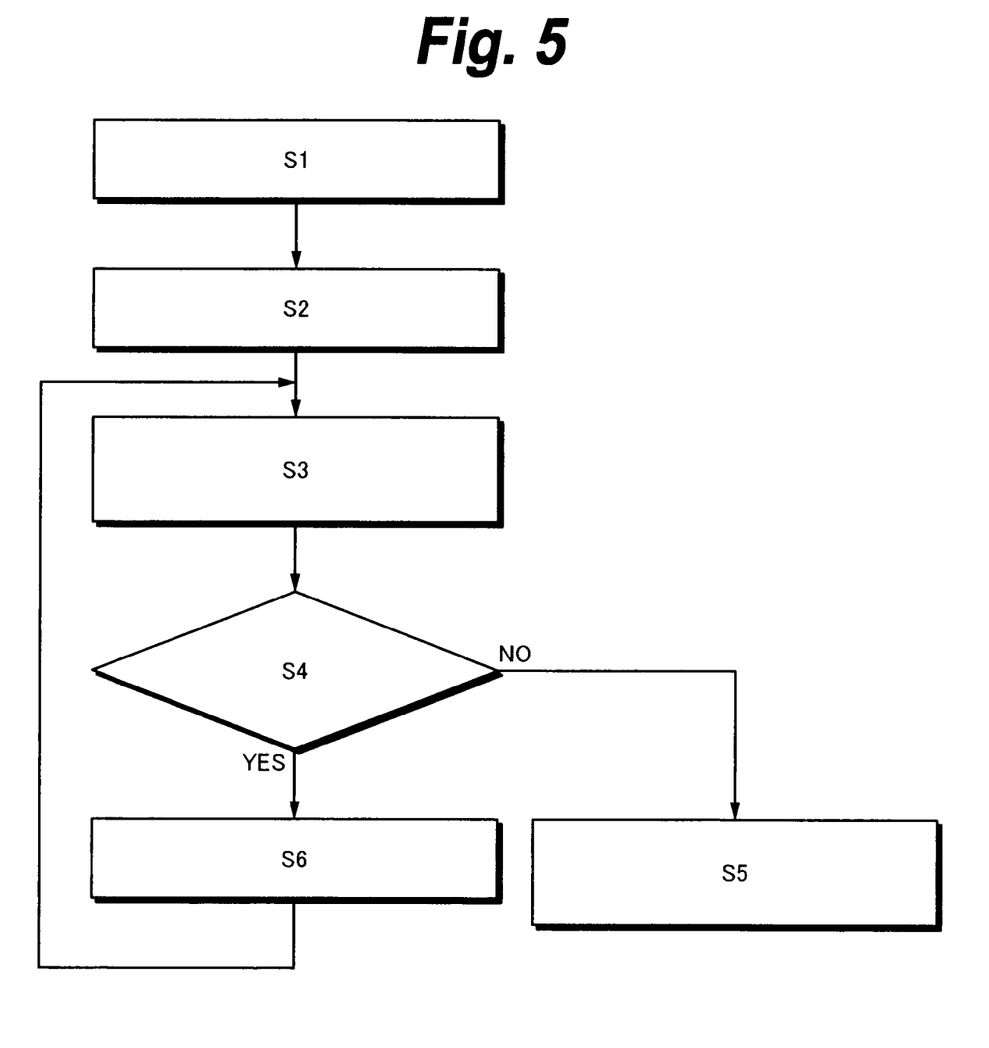
FIG. 5 is a flow chart showing a flow of a process under the control of a CPU of a content reproducing apparatus according to an embodiment of the present invention.

FIG. 5 is a flow chart showing a flow of a content reproduction process controlled by the CPU 3 according to this embodiment of the present invention. At step S1, the tempo detection section 9 detects a moving tempo. Since the user's moving tempo varies time by time, the tempo detection section 9 detects moving tempos, for example, for p seconds and treats their mean value as the user's moving tempo. When the moving tempo has been detected, the flow of the process advances to step S2.

At step S2, music content that is being reproduced is restored for X seconds. X seconds are, for example, five seconds to 10 seconds. If music content is not being reproduced, the process is not performed at step S2. Thereafter, the flow of the process advances to step S3.

At step S3, the play list selection process is performed. In the play list selection process, a play list corresponding to the detected moving tempo is selected from a plurality of play lists corresponding to individual tempos. Music content categorized as a highly ranked genre is selected and reproduced from those corresponding to the selected play list. Thereafter, the flow of the process advances to step S4.

At step S4, it is determined whether or not the difference between the moving tempo detected in the tempo detection section 9 and the tempo of the play list corresponding to the music content that is being reproduced is Y % or more. For example, it is determined whether or not the difference between the maximum value or the minimum value of the tempos of the play list selected at step S3 and the moving tempo is Y %. Value Y is properly set in a range where the moving tempo and the tempo of music content are acoustically recognized as the nearly same tempo. At step S4, it may be determined whether or not the difference between the maximum value or the minimum value of the tempos of the play list selected at step S3 and the moving tempo exceeds a predetermined threshold value, for example, 5 BPM, rather than the comparison of relative values. If the difference is smaller than Y %, the flow of the process advances to step S5.

At step S5, since the difference between the moving tempo and the tempo of the play list corresponding to the music content that is being reproduced does not exceed the predetermined value, the reproduction of the music content is continued. After the reproduction of the music content has been completed, music content that has the next highest reproduction order is selected from the play list selected at step S3 and reproduced.

If there is a difference of Y % at step S4, the flow of the process advances to step S6 where a new play list is selected. At step S6, the tempo detected in the tempo detection section 9 and meta information as tempos added to play lists stored in the play list database 8 are compared. Thereafter, the flow of the process advances to step S3 where a play list corresponding to the newly detected moving tempo is selected.

An embodiment of the present invention has been specifically described. However, the present invention is not limited to the foregoing embodiment. Instead, various modifications may be made based on the spirit of the present invention.

For example, if there are a plurality of music contents categorized as a higher priority genre in genre ranks (for example, music contents M407 and M408 categorized as a genre of rock in FIG. 4), these music contents may be reproduced at random or in the order of those having newer time information (year, month, day, hour, minute, etc.) that represents their registration times in the music content database 7. If music contents of the music content database 7 are ripped from an optical disc or the like, they may be reproduced in the order of which they were recorded on the optical disc (in the order of track numbers).

In addition, the content reproducing apparatus 1 may be of a console type rather than a portable type. The present invention may be applied not only to a dedicated audio reproducing apparatus, but to a portable reproducing apparatus having another function of mobile phone, PDA (Personal Digital Assistants), audio recording apparatus, a digital camera or the like.

In addition, in the foregoing embodiment, for example, it was described that play lists corresponding to tempos are created in advance. Instead, a play list may be adaptively created corresponding to a detected moving tempo. For example, the CPU 3 may select music contents having tempos that are different from the detected tempo by ±5 BPM from the music content database 7 and create a play list corresponding to the selected music contents. Music contents may be selected from the created play list in the order corresponding to rank information and the selected music contents may be reproduced.

In the foregoing embodiment, it was described that content is music content. Instead, the present invention can be applied to other contents such as videos, games, electronic books, still images, and so forth. In addition, genre ranks as exemplary rank information are created corresponding to types of contents. If contents are games, genres of "shooting", "adventure", "role playing", and so forth are created. If contents are electronic books, genres of "historical novels", "mystery stories", "comics", and so forth are created.

In addition, in the foregoing embodiment, it was described that play lists are created corresponding to tempos. Instead, the present invention can be applied to the case that play lists are created corresponding to genres, artists, years, and so forth.

In addition, rank information is not limited to genre ranks. Instead, rank information may be rank information categorized as years or artists. For example, rank information categorized as artists may be created such that priority of artists depends on how frequently their music contents have been reproduced.

In addition, in the foregoing embodiment, the CPU 3 has a structure that executes a play list creating process and a rank information creating process. Instead, two CPUs may be disposed to execute these processes, respectively.

In addition, each means that composes the reproducing apparatus of the present invention may be accomplished by a dedicated hardware circuit, a method, or a programmed computer. In addition, a program that describes contents of the processes may be recorded to a magnetic recording apparatus or a computer readable record medium such as an optical disc, a magneto-optical disc, or a semiconductor memory.

DESCRIPTION OF REFERENCE NUMERALS

1 CONTENT REPRODUCING APPARATUS
3 CPU
7 MUSIC CONTENT DATABASE

-continued

DESCRIPTION OF REFERENCE NUMERALS

8 PLAY LIST DATABASE
9 TEMPO DETECTION SECTION
12 DECODER AND AMPLIFIER SECTION
13 COMMUNICATION SECTION
14 HEAD PHONE
15 INTERNET
16 MUSIC CONTENT DELIVERY SERVER
S1 DETECT MOVING TEMPO BY AVERAGING MOVING TEMPOS FOR P SECONDS.
S2 CONTINUE TO REPRODUCE MUSIC CONTENT FOR X SECONDS.
S3 SELECT PLAY LIST CLOSE TO MOVING TEMPO. SELECT SONGS IN ORDER OF HIGHER GENRE RANKS FROM PLAY LIST AND REPRODUCE THEM.
S4 IS THERE DIFFERENCE BETWEEN MOVING TEMPO AND TEMPO OF PLAY LIST BEING REPRODUCED BY Y % OR MORE?
S5 REPRODUCE SONG AS IT IS. AFTER REPRODUCTION OF SONG HAS BEEN COMPETED, REPRODUCE NEXT SONG OF PLAY LIST.
S6 COMPARE MOVING TEMPO WITH TEMPO OF PLAY LIST.

The invention claimed is:

1. A content reproducing apparatus, comprising:
a computer configured to
store a plurality of contents;
create rank information based on a user's preference information, that is selected by a user, that prioritizes the plurality of contents based on a tempo and at least one of a genre, an artist, and a year;
store the rank information;
assign the plurality of contents to playlists to create the playlists, each of the playlists specifying a subset of the plurality of contents that have a common tempo;
reproduce the contents assigned to the plavlists in an order based on the rank information, the reproducing including reproducing one of the playlists as a currently reproduced playlist;
detect the user's moving tempo;
determine a percentage of difference between the user's moving tempo and a maximum or minimum tempo corresponding to the currently reproduced playlist, and only when the percentage of difference exceeds a predetermined threshold percentage value, select a new playlist corresponding to the user's moving tempo from the playlists; and
reproduce the subset of the plurality of contents assigned to the newly selected playlist.

2. The content reproducing apparatus as set forth in claim 1, wherein
the plurality of contents are at least one of music, sound, video, game, electronic book, and image content.

3. A content reproducing method, comprising:
a content storing step, implemented by a computer, for storing a plurality of contents;
a rank information creating step for creating rank information based on a user's preference information, that is selected by a user, that prioritizes the plurality of contents based on a tempo and at least one of a genre, an artist, and a year;
a rank information storage step for storing the rank information;
a playlist creating step for assigning the plurality of contents to playlists to create the playlists, each of the playlists specifying a subset of the plurality of contents that have a common tempo;

a reproduction controlling step for reproducing the contents assigned to the playlists in an order based on the rank information, the reproducing step including reproducing one of the playlists as a currently reproduced playlist;

a tempo detection step for detecting the user's moving tempo;

a determining step for determining a percentage of difference between the user's moving tempo and a maximum or minimum tempo corresponding to the currently reproduced playlist;

a selecting step for selecting, only when the difference exceeds a predetermined threshold percentage value, a new playlist corresponding to the user's moving tempo from the playlists; and a reproduction step of reproducing the subset of the plurality of contents assigned to the newly selected playlist.

4. A non-transitory computer readable storage medium having computer readable program codes embodied in the computer readable storage medium that, when executed, cause a computer to execute:

a content storing step for storing a plurality of contents;

a rank information creating step for creating rank information based on a user's preference information, that is selected by a user, that prioritizes the plurality of contents based on a tempo and at least one of a genre, an artist, and a year;

a rank information storage step for storing the rank information;

a playlist creating step for assigning the plurality of contents to playlists to create the playlists, each of the playlists specifying a subset of the plurality of contents that have a common tempo;

a reproduction controlling step for reproducing the contents assigned to the playlists in an order based on the rank information, the reproducing step including reproducing one of the playlists as a currently reproduced playlist;

a tempo detection step for detecting the user's moving tempo;

a determining step for determining a percentage of difference between the user's moving tempo and a maximum or minimum tempo corresponding to the currently reproduced playlist;

a selecting step for selecting, only when the difference exceeds a predetermined threshold percentage value, a new playlist corresponding to the user's moving tempo from the playlists; and a reproduction step of reproducing the subset of the plurality of contents assigned to the newly selected playlist.

5. The content reproducing apparatus as set forth in claim 1, wherein the user's moving tempo is determined based on a mean number of time intervals after one of the user's feet touches the ground and until the other of the user's feet touches the ground, within a predetermined time period.

6. The content reproducing apparatus as set forth in claim 1, wherein the common tempo is based on a mean number of quarter note beats within a predetermined time period.

7. The content reproducing apparatus as set forth in claim 1, wherein the computer includes at least one of an acceleration sensor, a speed sensor, a pressure sensor, a body motion acceleration sensor, and a position sensor.

8. The content reproducing apparatus as set forth in claim 1, wherein the computer is configured to detect the user's moving tempo based on biological information including at least one of: skin perspiration, skin resistance, muscle potential, or body surface temperature of the user.

9. The content reproducing method as set forth in claim 3, wherein a content reproducing apparatus creates the rank information by assigning a priority to each of the plurality of contents based on a frequency of reproduction.

10. The content reproducing method as set forth in claim 3, wherein a content reproducing apparatus creates the rank information by assigning a priority to each of the plurality of contents based on the number of contents classified in the same genre.

11. The content reproducing method as set forth in claim 3, wherein the user's preference information prioritizes a tempo.

12. The non-transitory computer readable storage medium as set forth in claim 4, wherein the user's preference information prioritizes a tempo.

* * * * *